United States Patent [19]

Suzuki

[11] Plant 3,996

[45] Dec. 21, 1976

[54] ROSE PLANT

[75] Inventor: Seizo Suzuki, Chiba, Japan

[73] Assignee: Jackson & Perkins Company, Medford, Oreg.

[21] Appl. No.: 628,115

[22] Filed: Nov. 3, 1975

[51] Int. Cl.[2] ..... A01H 5/00
[52] U.S. Cl. ..... Plt./2
[58] Field of Search ..... Plt./2

*Primary Examiner*—Robert E. Bagwill
*Attorney, Agent, or Firm*—Klarquist, Sparkman, Campbell, Leigh, Hall & Whinston

CLAIM

A new and distinct cultivar of rose plant of the Pillar class, substantially as herein shown and described, characterized particularly as to novelty by the unique combination of its vigorous growth, of its upright pillar form, with large clusters of blooms having between 25 to 30 petals in each bloom, and possessing a bloom color similar to that of cultivar Joseph's Coat.

1 Drawing Figure

This present invention relates to a new and distinct cultivar of rose plant of the pillar class which was originated by me by crossing an unnamed, undistributed cultivar, seedling of Joseph's Coat, U.S. Plant Pat No. 2,488, with pollen from an unnamed, undistributed cultivar of the floribunda class.

The primary objective of this breeding was to develop a new and improved cultivar of the pillar class similar to Joseph's Coat, but with improved flower form, substance, petalage and color.

This objective was fully achieved along with other desirable improvements as evidenced by the following unique combination of characteristics which are outstanding in the new cultivar and which distinguish it from its parents as well as from all other cultivars of which I am aware:

1. A vigorous, upright plant of pillar form, producing large clusters of blooms.
2. Buds and open flowers have a color similar to the cultivar Joseph's Coat, but have two to three times the number of petals per flower in a more imbricated form.

Asexual reproduction of this new cultivar by budding as performed at Wasco, Calif., shows that the aforementioned characteristics come true to form and are established and transmitted through succeeding propagations.

The accompanying illustration shows typical specimens of the vegetative growth and flowers of this new cultivar in different stages of development and as depicted in color as nearly true as it is reasonably possible to make the same in a color illustration of this character.

The following is a detailed description of my new rose cultivar with color terminology in accordance with Wilson's Horticultural Color Chart except where ordinary dictionary significance of color is indicated.

Parentage: Seedling.
*Seed parent.*—(Joseph's Coat × Arlene Francis).
*Pollen parent.*—[(Goldilocks × Golden Scepter) × Sarabande].

Classification:
*Botanical.*—Rosa hybrid.
*Commercial.*—Pillar.

FLOWER

Observations were made at Irvine, California, August 1975.

Blooming habit: Recurrent, continuous.

Bud:
*Size.*—¾" when petals start to unfurl.
*Form.*—Short, blunt top.
*Color.*—When sepals first divide Lemon Yellow (4/1), oldest exposed areas are between Vermilion (18) and Garnet Brown (00918). When half blown; upper side of petals mostly Lemon Yellow (4/1), outer edges show increasing amounts of a color between Vermilion (18) and Garnet Brown (00918) as the flower matures. Lower side of petals Lemon Yellow (4/1) with some areas of outer petals between Vermilion (18) and Garnet Brown (00918).
*Sepals.*—Color: Outer surface near Spinach Green (0960/3) with irregular areas of near Garnet Brown (00918/3)—many stipitate glands on outer surface of sepals. Inner surface somewhat lighter than outer surface and moderately covered with white tomentum. Three appendaged sepals normally appendaged. Two unappendaged sepals hairy edged.
*Receptacle.*—Color: Near Spinach Green (0960/3). Shape: Apple, with broad distal end. Size: Large, relative to bud size. Surface: Smooth.
*Peduncle.*—Length: Short. Surface: Prickly and glandular with stipitate glands. Color: Light green. Strength: Stiff, erect.
*Opening.*—Petals unfold with little curling until well opened.

Bloom:
*Size.*—Medium. Average open size 2½".
*Borne.*—In rounded clusters.
*Stems.*—Short stems in clusters which are borne on long canes.
*Form.*—When first open, high centered. Permanence: Retains its form to the end, outer petal edges slightly curled.
*Petalage.*—Number of petals under normal conditions 25–30.
*Color.*—Center of flower: Upper side of petals near Indian Yellow (6), outer portions of petals lightly overlaid with a color near Vermilion (18). Reverse side of petals near Empire Yellow (603). Base of petals near Lemon Yellow (4/1). General tonality from a distance Indian Yellow (6) overlaid with Vermilion (717).

*Discoloration.*—Where petal surface is exposed to sun, color changes to a color between Dutch Vermilion (717) and Garnet Brown (00918/3). Where petal surface is shaded by another petal above it, it remains yellow. Third day—exposed petal surfaces become slightly darker.

Petals:

*Texture.*—Thick.
*Shape.*—Nearly round.
*Form.*—Slightly recurved.
*Arrangement.*—Imbricated.
*Persistence.*—Drop off cleanly.
*Fragrance.*—Slight, Zinnia like.
*Lastingness.*—On the plant—long. As cut flower—fair.

Reproductive parts:

*Stamens, Anthers.*—Large, many. Color—Yellow. Arrangement—regular around styles.
*Filaments (threads).*—Color—Yellow.
*Pollen.*—Gold Yellow.
*Styles.*—Color—Chartreuse Green (663).
*Stigmas.*—Color—Chartreuse Green (663).

PLANTS

Form: Pillar.

Growth: Vigorous, upright, branching. Blooms mostly in round topped clusters of 15 or more blooms.

Foilage: Number of leaflets on normal mid-stem leaves —5.

*Size.*—Large.
*Quantity.*—Abundant.
*Color.*—New Foliage: Parsley Green (00962/3), lightly overlaid at very early stages with Garnet Brown (00918/3). Old Foliage: Near Parsley Green (00962/3).

*Shape.*—Oval pointed.
*Texture.*—Leathery.
*Edge.*—Serrated.
*Serration.*—Single.
*Petiole.*—Rachis—Color—Green. Underside—prickles.
*Stipules.*—Long.

Wood:

*New Wood.*—Color—Garnet Brown (00918/3). Bark—Smooth.
*Old Wood.*—Color—Green, Garnet Brown where most exposed to sun. Bark—Smooth.

Prickles:

*Quantity.*—On main stalks from base—many. On laterals from stalk—many.
*Form.*—Narrow based, medium, hooked downwardly.
*Color when young.*—Red.
*Position.*—Irregular.

Small Prickles:

*Quantity.*—On main stalks—many. On laterals —many.
*Color.*—Brown.

I claim:

1. A new and distinct cultivar of rose plant of the Pillar class, substantially as herein shown and described, characterized particularly as to novelty by the unique combination of its vigorous growth, of its upright pillar form, with large clusters of blooms having between 25 to 30 petals in each bloom, and possessing a bloom color similar to that of the cultivar Joseph's Coat.

* * * * *

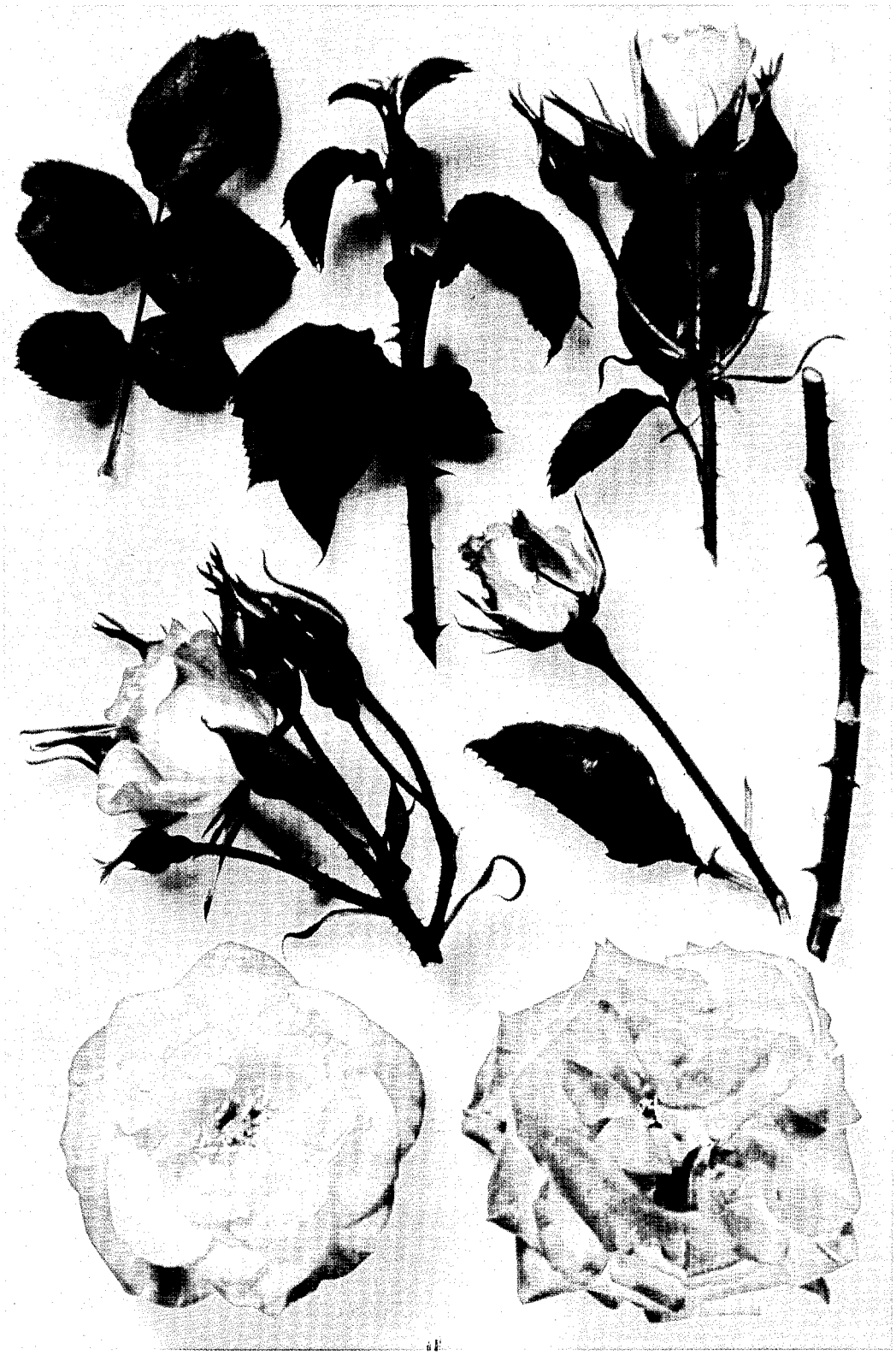

Dec. 21, 1976 S. SUZUKI Plant Pat. 3,996
ROSE PLANT
Filed Nov. 3, 1975